US005541110A

United States Patent [19]

Siegall

[11] Patent Number: 5,541,110
[45] Date of Patent: Jul. 30, 1996

[54] **CLONING AND EXPRESSION OF A GENE ENCODING BRYODIN 1 FROM *BRYONIA DIOICA***

[75] Inventor: Clay B. Siegall, Edmonds, Wash.

[73] Assignee: Bristol-Myers Squibb, New York, N.Y.

[21] Appl. No.: 245,754

[22] Filed: May 17, 1994

[51] Int. Cl.[6] .............................. C12N 1/20; C12N 15/63; C12N 9/22; C07H 21/04; C07K 14/00

[52] U.S. Cl. .................................... 435/252.3; 435/320.1; 435/199; 536/23.2; 536/23.6; 530/350

[58] Field of Search .................................. 435/69.1, 199, 435/320.1, 252.3; 536/23.2, 23.6; 530/350

[56] References Cited

FOREIGN PATENT DOCUMENTS

| | | | |
|---|---|---|---|
| 0390040 | 3/1990 | European Pat. Off. ........ | C07K 15/14 |
| 2194948 | 8/1987 | United Kingdom ........... | C07K 15/00 |
| WO91/00295 | 1/1991 | WIPO ............................ | C07K 15/28 |

OTHER PUBLICATIONS

C. Z. Amorim et al., "Screening of the Antimalarial Activity of Plants of the Cucurbitaceae Family," *Mem. Inst. Oswaldo Cruz* 86:177–180, 1991.

Y. Endo et al., "RNA N–Glycosidase Activity of Ricin A–chain," *J. Biol. Chem.* 262:8128–8130, 1987.

P.–C. Montecucchi et al., "N–terminal sequence of some ribosome–inactivating proteins," *Int. J. Peptide Protein Res.* 33:263–267, 1989.

T. B. Ng et al., "Proteins with abortifacient, ribosome in activating, immunomodulatory, antitumor and anti–AIDS activities from Cucurbitaceae plants," *Gen. Pharmac.* 23:575–590, 1992.

F. Stirpe et al., "Bryodin, a ribosome–inactivating protein from the roots of *Bryonia dioica* L. (white bryony)," *Biochem. J.* 240:659–665, 1986.

F. Stirpe et al., "Modification of ribosomal RNA by ribosome–inactivating proteins from plants," *Nucleic Acids Research* 16:1349–1357, 1988.

*Primary Examiner*—Robert A. Wax
*Assistant Examiner*—Kawai Lau

[57] ABSTRACT

The molecular cloning and expression of biologically active ribosome-inactivating protein bryodin 1 are described. A complete amino acid and oligonucleotide sequence encoding bryodin 1 are also described. Further, plasmids, expression vectors comprising a nucleotide sequence encoding bryodin 1 and transformed host cells are described. Isolation and characterization of the nucleotide sequence for bryodin 1 enables the recombinant production of large amount of bryodin 1 for use in vitro or in vivo directly or as ligand/toxin conjugates or fusion proteins. These compositions can be used to selectively kill undesired cells such as cancer cells, infected cells, bacteria.

11 Claims, 9 Drawing Sheets

```
                                                      TCATCGAAATTCATCAAGACTGAATTGAAAGAGTAAAAAAAAA         43
                                                                                        ↓
                                 10                                    20
Met Ile Lys Leu Leu Val Leu Trp Leu Leu Ile Leu Thr Ile Phe Leu Lys Ser Pro Thr Val Glu Gly Asp Val
ATG ATC AAA TTG TTA GTC CTT TGG TTG CTA ATT CTC ACC ATA TTC CTC AAA TCT CCA ACT GTT GAG GGC GAT GTT   118
                                 35                                    45
Ser Phe Arg Leu Ser Gly Ala Thr Thr Thr Ser Tyr Gly Val Phe Ile Lys Asn Leu Arg Glu Ala Leu Pro Tyr
AGC TTC CGT TTA TCA GGT GCT ACA ACC ACA TCC TAT GGA GTT TTC ATT AAA AAT CTG AGA GAA GCT CTT CCA TAC   193
                                 60                                    70
Glu Arg Lys Val Tyr Asn Ile Pro Leu Leu Arg Ser Ser Ile Ser Gly Ser Gly Arg Tyr Thr Leu Leu His Leu
GAA AGG AAA GTG TAC AAT ATA CCG CTA TTA CGT TCA AGT ATT TCA GGT TCA GGA CGC TAC ACA TTA CTC CAT CTC   268
                                 85                                    95
Thr Asn Tyr Ala Asp Glu Thr Ile Ser Val Ala Val Asp Val Thr Asn Val Tyr Ile Met Gly Tyr Leu Ala Gly
ACA AAT TAC GCG GAT GAA ACC ATC TCA GTG GCA GTA GAC GTA ACA AAC GTC TAT ATT ATG GGG TAT CTT GCC GGT   343
                                110                                   120
Asp Val Ser Tyr Phe Phe Asn Glu Ala Ser Ala Thr Glu Ala Ala Lys Phe Val Phe Lys Asp Ala Lys Lys Lys
GAT GTG TCC TAT TTT TTC AAC GAG GCT TCA GCA ACA GAA GCT GCA AAA TTC GTA TTC AAA GAT GCT AAG AAA AAA   418
                                135                                   145
Val Thr Leu Pro Tyr Ser Gly Asn Tyr Glu Arg Leu Gln Thr Ala Ala Gly Lys Ile Arg Glu Asn Ile Pro Leu
GTG ACG CTT CCA TAT TCA GGC AAT TAC GAA AGG CTT CAA ACT GCT GCA GGA AAA ATA AGA GAA AAT ATT CCA CTT   493
                                160                                   170
Gly Leu Pro Ala Leu Asp Ser Ala Ile Thr Thr Leu Tyr Tyr Tyr Thr Ala Ser Ser Ala Ala Ser Ala Leu Leu
GGA CTC CCA GCT TTG GAC AGT GCC ATT ACC ACT TTG TAT TAC TAC ACC GCC AGT TCT GCG GCT TCT GCA CTT CTT   568
                                185                                   195
Val Leu Ile Gln Ser Thr Ala Glu Ser Ala Arg Tyr Lys Phe Ile Glu Gln Gln Ile Gly Lys Arg Val Asp Lys
GTA CTC ATT CAA TCC ACG GCT GAA TCT GCA AGG TAT AAA TTT ATT GAA CAA CAA ATT GGA AAG CGT GTA GAC AAA   643
                                210                                   220
Thr Phe Leu Pro Ser Leu Ala Thr Ile Ser Leu Glu Asn Asn Trp Ser Ala Leu Ser Lys Gln Ile Gln Ile Ala
ACT TTT TTA CCA AGT TTA GCA ACT ATT AGT TTG GAA AAT AAT TGG TCT GCT CTG TCC AAG CAA ATT CAG ATA GCC   718
                                235                                   245
Ser Thr Asn Asn Gly Gln Phe Glu Ser Pro Val Val Leu Ile Asp Gly Asn Asn Gln Arg Val Ser Ile Thr Asn
AGT ACC AAT AAT GGA CAA TTT GAG AGT CCT GTT GTG CTT ATA GAT GGT AAC AAC CAA CGA GTC TCT ATA ACC AAT   793
                                260                                   270↓F2
Ala Ser Ala Arg Val Val Thr Ser Asn Ile Ala Leu Leu Leu Asn Arg Asn Asn Ile Ala Ala Ile Gly Glu Asp
GCT AGT GCT CGA GTT GTA ACC TCC AAC ATA GCG TTG CTG CTA AAC AGA AAT AAT ATT GCA GCC ATT GGA GAG GAC   868
                                285                  ↓F1
Ile Ser Met Thr Leu Ile Gly Phe Glu His Gly Leu Tyr Gly Ile
ATT TCT ATG ACA CTC ATC GGC TTT GAA CAT GGA CTT TAT GGT ATA TAG TGTAAGTTTAAAGCTATGGACAAGCACAAACTCCA   951

CCTGAAGAACAATCTGTTGTTCTTCGAGAGGTTAATCTACTTGTATAAATAAAGAATGTTCATGTGATCTATCTACGTTAATTCTGTCTGTTGTTGTTG   1050
CTTTAAATAATAAAAGTGTGGAGTCCTTCTATAAAAAAAAAAA                                                         1094
```

Figure 5

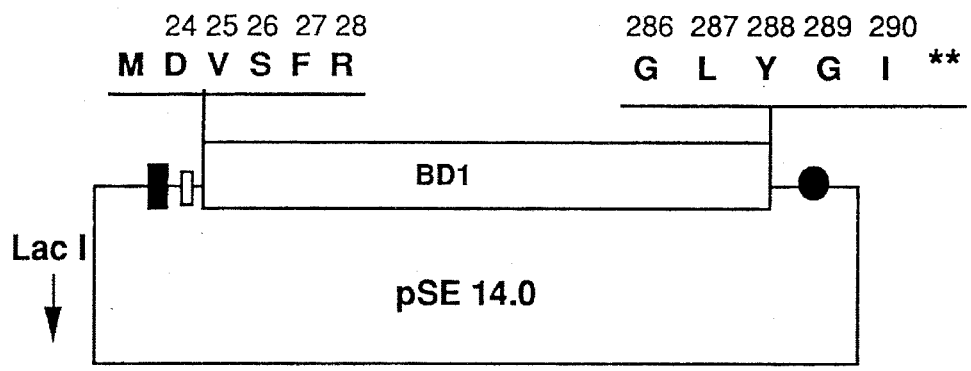
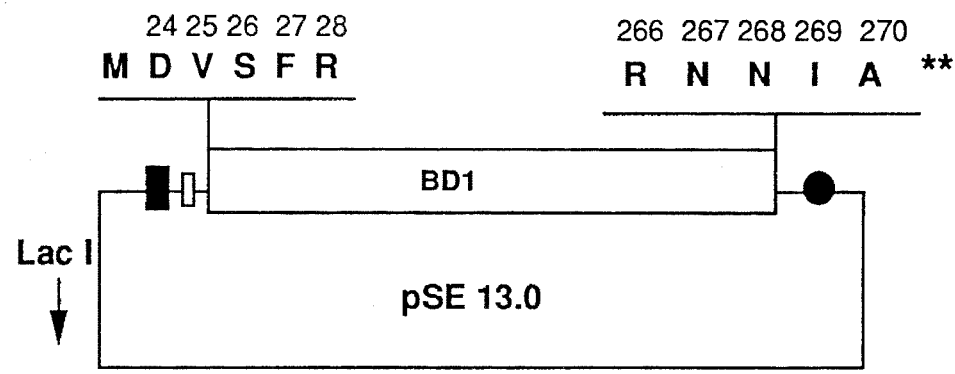
■ = T7 promoter
** = Stop Codon x 2
☐ = lac operator
● = T7 terminator
Figure 6

SEQUENCE LISTING ( 1 ) GENERAL INFORMATION:

( i i i ) NUMBER OF SEQUENCES: 16

( 2 ) INFORMATION FOR SEQ ID NO:1:

( i ) SEQUENCE CHARACTERISTICS:
        ( A ) LENGTH: 1094 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( v i ) ORIGINAL SOURCE:
        ( A ) ORGANISM: Bryonia dioica ( x i ) SEQUENCE DESCRIPTION: SEQ ID NO:1:

```
TCATCGAAAT TCATCAAGAC TGAATTGAAA GAGTAAAAAA AAAATGATCA AATTGTTAGT     60
CCTTTGGTTG CTAATTCTCA CCATATTCCT CAAATCTCCA ACTGTTGAGG GCGATGTTAG    120
CTTCCGTTTA TCAGGTGCTA CAACCACATC CTATGGAGTT TTCATTAAAA ATCTGAGAGA    180
AGCTCTTCCA TACGAAAGGA AAGTGTACAA TATACCGCTA TTACGTTCAA GTATTTCAGG    240
TTCAGGACGC TACACATTAC TCCATCTCAC AAATTACGCG GATGAAACCA TCTCAGTGGC    300
AGTAGACGTA ACAAACGTCT ATATTATGGG GTATCTTGCC GGTGATGTGT CCTATTTTTT    360
CAACGAGGCT TCAGCAACAG AAGCTGCAAA ATTCGTATTC AAAGATGCTA AGAAAAAAGT    420
GACGCTTCCA TATTCAGGCA ATTACGAAAG GCTTCAAACT GCTGCAGGAA AAATAAGAGA    480
AAATATTCCA CTTGGACTCC CAGCTTTGGA CAGTGCCATT ACCACTTTGT ATTACTACAC    540
CGCCAGTTCT GCGGCTTCTG CACTTCTTGT ACTCATTCAA TCCACGGCTG AATCTGCAAG    600
GTATAAATTT ATTGAACAAC AAATTGGAAA GCGTGTAGAC AAAACTTTTT TACCAAGTTT    660
AGCAACTATT AGTTTGGAAA ATAATTGGTC TGCTCTGTCC AAGCAAATTC AGATAGCCAG    720
TACCAATAAT GGACAATTTG AGAGTCCTGT TGTGCTTATA GATGGTAACA ACCAACGAGT    780
CTCTATAACC AATGCTAGTG CTCGAGTTGT AACCTCCAAC ATAGCGTTGC TGCTAAACAG    840
AAATAATATT GCAGCCATTG GAGAGGACAT TTCTATGACA CTCATCGGCT TTGAACATGG    900
ACTTTATGGT ATATAGTGTA AGTTTAAAGC TATGGACAAG CACAAACTCC ACCTGAAGAA    960
CAATCTGTTG TTCTTCGAGA GGTTAATCTA CTTGTATAAA TAAGAATGT TCATGTGATC   1020
TATCTACGTT AATTCTGTCT GTTGTTGTTG CTTTAAATAA TAAAAAGTGT GGAGTCCTTC   1080
TATAAAAAAA AAAA                                                     1094
```

( 2 ) INFORMATION FOR SEQ ID NO:2:

( i ) SEQUENCE CHARACTERISTICS:
        ( A ) LENGTH: 290 amino acids
        ( B ) TYPE: amino acid
        ( D ) TOPOLOGY: linear ( i i ) MOLECULE TYPE: protein ( v ) FRAGMENT TYPE: N-terminal ( v i ) ORIGINAL SOURCE:
        ( A ) ORGANISM: Bryonia dioica ( x i ) SEQUENCE DESCRIPTION: SEQ ID NO:2:

| Met | Ile | Lys | Leu | Leu | Val | Leu | Trp | Leu | Leu | Ile | Leu | Thr | Ile | Phe | Leu |
|---|---|---|---|---|---|---|---|---|---|---|---|---|---|---|---|
| 1 | | | | 5 | | | | | 10 | | | | | 15 | |

| Lys | Ser | Pro | Thr | Val | Glu | Gly | Asp | Val | Ser | Phe | Arg | Leu | Ser | Gly | Ala |
|---|---|---|---|---|---|---|---|---|---|---|---|---|---|---|---|
| | | | 20 | | | | | 25 | | | | | 30 | | |

| Thr | Thr | Thr | Ser | Tyr | Gly | Val | Phe | Ile | Lys | Asn | Leu | Arg | Glu | Ala | Leu |
|---|---|---|---|---|---|---|---|---|---|---|---|---|---|---|---|
| | | 35 | | | | | 40 | | | | | 45 | | | |

| Pro | Tyr | Glu | Arg | Lys | Val | Tyr | Asn | Ile | Pro | Leu | Leu | Arg | Ser | Ser | Ile |
|---|---|---|---|---|---|---|---|---|---|---|---|---|---|---|---|
| | 50 | | | | | 55 | | | | | 60 | | | | |

| Ser | Gly | Ser | Gly | Arg | Tyr | Thr | Leu | Leu | His | Leu | Thr | Asn | Tyr | Ala | Asp |
|---|---|---|---|---|---|---|---|---|---|---|---|---|---|---|---|
| 65 | | | | | 70 | | | | | 75 | | | | | 80 |

| Glu | Thr | Ile | Ser | Val | Ala | Val | Asp | Val | Thr | Asn | Val | Tyr | Ile | Met | Gly |
|---|---|---|---|---|---|---|---|---|---|---|---|---|---|---|---|
| | | | | 85 | | | | | 90 | | | | | 95 | |

| Tyr | Leu | Ala | Gly | Asp | Val | Ser | Tyr | Phe | Phe | Asn | Glu | Ala | Ser | Ala | Thr |
|---|---|---|---|---|---|---|---|---|---|---|---|---|---|---|---|
| | | | 100 | | | | | 105 | | | | | 110 | | |

| Glu | Ala | Ala | Lys | Phe | Val | Phe | Lys | Asp | Ala | Lys | Lys | Val | Thr | Leu |
|---|---|---|---|---|---|---|---|---|---|---|---|---|---|---|
| | | 115 | | | | | 120 | | | | | 125 | | |

| Pro | Tyr | Ser | Gly | Asn | Tyr | Glu | Arg | Leu | Gln | Thr | Ala | Ala | Gly | Lys | Ile |
|---|---|---|---|---|---|---|---|---|---|---|---|---|---|---|---|
| | 130 | | | | | 135 | | | | | 140 | | | | |

| Arg | Glu | Asn | Ile | Pro | Leu | Gly | Leu | Pro | Ala | Leu | Asp | Ser | Ala | Ile | Thr |
|---|---|---|---|---|---|---|---|---|---|---|---|---|---|---|---|
| 145 | | | | | 150 | | | | | 155 | | | | | 160 |

| Thr | Leu | Tyr | Tyr | Tyr | Thr | Ala | Ser | Ser | Ala | Ala | Ser | Ala | Leu | Leu | Val |
|---|---|---|---|---|---|---|---|---|---|---|---|---|---|---|---|
| | | | | 165 | | | | | 170 | | | | | 175 | |

| Leu | Ile | Gln | Ser | Thr | Ala | Glu | Ser | Ala | Arg | Tyr | Lys | Phe | Ile | Glu | Gln |
|---|---|---|---|---|---|---|---|---|---|---|---|---|---|---|---|
| | | | 180 | | | | | 185 | | | | | 190 | | |

| Gln | Ile | Gly | Lys | Arg | Val | Asp | Lys | Thr | Phe | Leu | Pro | Ser | Leu | Ala | Thr |
|---|---|---|---|---|---|---|---|---|---|---|---|---|---|---|---|
| | | 195 | | | | | 200 | | | | | 205 | | | |

| Ile | Ser | Leu | Glu | Asn | Asn | Trp | Ser | Ala | Leu | Ser | Lys | Gln | Ile | Gln | Ile |
|---|---|---|---|---|---|---|---|---|---|---|---|---|---|---|---|
| | 210 | | | | | 215 | | | | | 220 | | | | |

| Ala | Ser | Thr | Asn | Asn | Gly | Gln | Phe | Glu | Ser | Pro | Val | Val | Leu | Ile | Asp |
|---|---|---|---|---|---|---|---|---|---|---|---|---|---|---|---|
| 225 | | | | | 230 | | | | | 235 | | | | | 240 |

| Gly | Asn | Asn | Gln | Arg | Val | Ser | Ile | Thr | Asn | Ala | Ser | Ala | Arg | Val | Val |
|---|---|---|---|---|---|---|---|---|---|---|---|---|---|---|---|
| | | | | 245 | | | | | 250 | | | | | 255 | |

| Thr | Ser | Asn | Ile | Ala | Leu | Leu | Leu | Asn | Arg | Asn | Asn | Ile | Ala | Ala | Ile |
|---|---|---|---|---|---|---|---|---|---|---|---|---|---|---|---|
| | | | 260 | | | | | 265 | | | | | 270 | | |

| Gly | Glu | Asp | Ile | Ser | Met | Thr | Leu | Ile | Gly | Phe | Glu | His | Gly | Leu | Tyr |
|---|---|---|---|---|---|---|---|---|---|---|---|---|---|---|---|
| | | 275 | | | | | 280 | | | | | 285 | | | |

| Gly | Ile |
|---|---|
| | 290 |

( 2 ) INFORMATION FOR SEQ ID NO:3:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:3:

CCTAGCCCAT GGATGTKAGC TTYCGTTT        28

( 2 ) INFORMATION FOR SEQ ID NO:4:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:4:

CCTAGCGAAT TCCTASAGAG GKATRTTGTA SAC                33

( 2 ) INFORMATION FOR SEQ ID NO:5:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:5:

TTATCAGGTG CTACAACCAC ATCC                24

( 2 ) INFORMATION FOR SEQ ID NO:6:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:6:

GAAGCTCTTC CATACGAAAG G                21

( 2 ) INFORMATION FOR SEQ ID NO:7:

( i ) SEQUENCE CHARACTERISTICS:
        ( A ) LENGTH: 75 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:7:

CAAAGATCCT CTGAATTCTT ACTATATACC ATAAAGTCCA TGTTCAAAGC CGATGAGTGT                60

CATAGAAATG TCCTC                75

( 2 ) INFORMATION FOR SEQ ID NO:8:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:8:

GAGAGGTATG TTGTAGACTT TCCT                24

( 2 ) INFORMATION FOR SEQ ID NO:9:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:9:

GACTCGAGTC GACATCGATT TTTTTTTTTT TTTTT      35

( 2 ) INFORMATION FOR SEQ ID NO:10:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:10:

GACTCGAGTC GACATCG      17

( 2 ) INFORMATION FOR SEQ ID NO:11:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: misc_feature
        ( B ) LOCATION: 23..24
        ( D ) OTHER INFORMATION: /note="N represents inosine ( i x ) FEATURE:
        ( A ) NAME/KEY: misc_feature
        ( B ) LOCATION: 24..25
        ( D ) OTHER INFORMATION: /note="N represents inosine ( i x ) FEATURE:
        ( A ) NAME/KEY: misc_feature
        ( B ) LOCATION: 29..30
        ( D ) OTHER INFORMATION: /note="N represents inosine ( i x ) FEATURE:
        ( A ) NAME/KEY: misc_feature
        ( B ) LOCATION: 30..31
        ( D ) OTHER INFORMATION: /note="N represents inosine ( i x ) FEATURE:
        ( A ) NAME/KEY: misc_feature
        ( B ) LOCATION: 34..35
        ( D ) OTHER INFORMATION: /note="N represents inosine ( i x ) FEATURE:
        ( A ) NAME/KEY: misc_feature
        ( B ) LOCATION: 35..36
        ( D ) OTHER INFORMATION: /note="N represents inosine ( x i ) SEQUENCE DESCRIPTION: SEQ ID NO:11:

GGCCACGCGT CGACTAGTAC GGGNNGGGNN GGGNNG      36

( 2 ) INFORMATION FOR SEQ ID NO:12:

( i ) SEQUENCE CHARACTERISTICS:
        ( A ) LENGTH: 56 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:12:

GTCAGAGTTC CATGGATGTG AGCTTTCGTT TATCAGGTGC TACAACCACA TCCTAT      56

(2) INFORMATION FOR SEQ ID NO:13:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:13:

CAAAGATCCT CTGAATTCTT ATTATGCAAT ATTATTTCTG TTAGCAGCAA     50

(2) INFORMATION FOR SEQ ID NO:14:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:14:

CTAGAAATAA TTTTGTTTAA CTTTAAGAAG GAGATAC     37

(2) INFORMATION FOR SEQ ID NO:15:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:15:

CATGGTATCT CCTTCTTAAA GTTAAACAAA ATTATTT     37

(2) INFORMATION FOR SEQ ID NO:16:

(i) SEQUENCE CHARACTERISTICS:
        (A) LENGTH: 75 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:16:

CAAAGATCCT CTGAATTCTT ACTATATACC ATAAAGTCCA TGTTCAAAGC CGATGAGTGT     60

CATAGAAATG TCCTC     75

CLONING AND EXPRESSION OF A GENE ENCODING BRYODIN 1 FROM *BRYONIA DIOICA*

FIELD OF THE INVENTION

The present invention relates to the isolation and characterization of an oligonucleotide sequence encoding a ribosome-inactivating protein from the plant *Bryonia dioica*. The invention also relates to expression vectors comprising the purified oligonucleotide sequence operatively linked with appropriate transcriptional and translational control sequences, transformed host cells and a recombinantly expressed ribosome-inactivating protein. Use of purified oligonucleotides encoding the ribosome-inactivating protein for the expression of a ribosome-inactivating protein (RIP) and in the construction of fusion proteins is also considered part of the present invention.

BACKGROUND OF THE INVENTION

Proteins which inhibit protein synthesis have been isolated from various organisms including plants, bacteria and fungi. These protein toxins are thought to be produced by the organisms in order to provide a selective advantage for the growth of the organisms that produce them. Despite the divergent evolutionary background of the organisms in which these protein toxins are found, most toxins have strikingly similar mechanisms of action. One particular group of toxins exerts its action by blocking protein synthesis either by directly modifying elongation factor 2 (EF-2) or by modifying the ribosome itself so that EF-2 cannot function in protein synthesis. This class of toxins, ribosome-inactivating proteins (RIPs), can be isolated from plants of several families.

Plant ribosome-inactivating proteins have been divided into two groups based on their structure. Type I ribosome-inactivating proteins (type I RIPs) contain a single chain that has ribosome-inactivating activity. Examples of type I RIPs include gelonin, saporin, trichosanthin and bryodin. Type II ribosome-inactivating proteins (type II RIPs) are comprised of two chains, an A chain that is able to inactivate EF-2, and a B chain, that contains a cell binding domain having lectin-like properties. The binding domain enables type II RIPs to bind many cell types and to kill those cells. Examples of type II RIPs are ricin and abrin.

Although the two types of ribosome-inactivating proteins differ in their structures, both types inhibit protein synthesis by inactivating the 60S subunit of eukaryotic ribosomes through cleavage of the N-glycosidic bond of the adenine residue at position 4324 of 28 S rRNA (Endo and Tsurugi 1987, *J. Biol. Chem.* 262:8128–8130; Stirpe, F. et al. 1988, *Nucl. Acid Res.* 16:1349–1357).

Ribosome-inactivating proteins have been isolated from several families of plants including the Cariophyllaceae, Cucurbitaceae, Euphorbiateae and Phytolaccaceae. The toxins have been isolated particularly from the root, seeds and leaves of the plants. Comparisons have been made of the N-terminal amino acid sequences of RIPs isolated from the seeds of *Gelonium multiflorum* (Euphorbiaceae), *Momordica charantia* (Cucurbitaceae), *Bryonia dioica* (Cucurbitaceae), *Saponaria officinalis* (saporin-5a, saporin-5b, saporin-6a, saporin-6b) (Cariophyllaeeae) and from the leaves of *Saponaria officinalis* (saporin-1). Complete amino acid sequences have been determined for a Type I RIP from *Trichosanthes kirilowii* maxim and from Barley seed protein synthesis inhibitor. These comparisons show that at least the N-terminal regions of the toxins bryodin and momordin (members of the Curcurbitaceae family) show a high level of similarity with ricin A chain and with gelonin which are members of the Euphorbiaceae family. The similarity is thought to be a consequence of a similar evolutionary origin. Very little similarity was found between RIPs of the Cucurbitaceae and Euphorbiaceae families and those of the Phytolaccaceae or Cariophyllaceae families (Montecucchi et al., 1989, *Int. J. Peptide Protein Res.* 33:263–267). Although similarities are found in the amino acid sequences of the N-terminal regions of RIPs isolated from the same species, many differences do exist particularly between toxins isolated from different tissue of the same plant.

A plant protein toxin designated bryodin was initially identified as a 27–30 kDa protein isolated from the root of *Bryonia dioica* (United Kingdom Patent Application GB2194948, published Mar. 23, 1988). The toxin is a type I ribosome-inactivating protein having a single chain and a mechanism of action which inactivates ribosomes by blocking productive interactions with elongation factor-2. In not having a cell binding domain, bryodin, like the other type I RIPs, does not normally bind to mammalian cells. The protein has been shown to have a molecular weight by gel filtration of about 27,300 daltons and about 28,800 daltons by polyacrylamide gel electrophoresis, and an isoelectric point of 9.5. This toxin was found to inhibit protein synthesis in the rabbit reticulocyte lysate system with wheat germ ribosomes at 3.6 ng/ml ($ID_{50}$) and an $LD_{50}$ in mice of 14.5 mg/kg when administered intraperitoneally. A complete nucleotide sequence has not been determined for bryodin 1 and only a partial N-terminal amino acid sequence has been obtained. The N-terminal amino acid sequence has been determined to be

```
                5                    10                    15
Asp—Val—Ser—Phe—Arg—Leu—Ser—Gly—Ala—Thr—Thr—Thr—Ser—Tyr—Gly—Val—
                20                   25                    30
Phe—Ile—Lys—Asn—Leu—Arg—Glu—Ala—Leu—Pro—Tyr—Glu—Arg—Lys—Val—Tyr—
                35                   40
Asn—Ile—Pro—Leu—Leu—Leu—Arg—His—Xxx—Ile—Gly—       (Seq. I.D.#2)
```

A second ribosome-inactivating protein has been isolated from the leaves of *B. dioica* (European Patent Publication EPO 390 040, published Oct. 3, 1990). This molecule has been described as having a molecular weight of 27,300 daltons by gel filtration and 28,800 daltons by polyacrylamide gel electrophoresis, and an isoelectric point of 9.5 and has been designated bryodin-L. This form of bryodin was found to inhibit protein synthesis in a rabbit reticulocyte lysate system with an $EC_{50}$ of 0.1 nM (3.6 ng/ml) and has an $LD_{50}$ in mice of 10 mg/kg when administered intraperitoneally. An amino acid analysis was also provided, but no amino acid sequence or nucleotide sequence for the molecules has been disclosed.

Ribosome-inactivating proteins are of interest because of their usefulness as components of "immunotoxins." Immunotoxins are hybrid molecules consisting of a toxic moiety linked to an antibody capable of selectively directing the toxin to a specific target cell. Potential target cells include harmful cells, i.e., neoplastic, virally infected, immunocompetent or parasitic cells. Immunotoxins as defined in the present invention can be chemical conjugates of a cell-specific ligand linked to a toxic molecule, such as a ribosome-inactivating protein. The fact that many different ribosome-inactivating proteins are known and that new toxins are being discovered provides a variety of toxic moieties which have varying levels of intrinsic toxicity on whole cells when unconjugated and provide an available source of alternative toxins should the patient develop an immune response during long term in vivo treatment to the originally administered immunotoxin. In addition, some immunotoxins, saporin 6 and an anti-Thy 1.1 antibody or its F(ab')$_2$ fragment, were more toxic than free toxin providing a need for new and different toxin molecules.

The present invention provides a purified oligonucleotide sequence encoding a plant protein toxin isolated from *Bryonia dioica*. Also, the present invention provides expression vectors wherein the purified oligonucleotide sequence is operatively linked with host cells appropriate transcriptional and translational control sequences which, when used to transform the appropriate host cells, express large amounts of the plant protein toxin. Further, the oligonucleotide sequence can be used to construct oligonucleotide molecules which encode fusion molecules comprising the toxin and a ligand specific for a target cell. This immunoconjugate is toxic to the target cell and provides compositions useful for directed cell killing.

SUMMARY OF THE INVENTION

The complete nucleotide sequence encoding the ribosome-inactivating protein bryodin 1 (BD1) isolated from the plant *Bryonia dioica* is disclosed herein, and provides from the basis of the present invention. The invention includes embodiments which disclose a purified oligonucleotide which encodes bryodin 1. Also, embodiments are included which disclose plasmids which comprise the DNA sequence which encodes bryodin 1 and expression vectors which comprise the DNA sequence which encodes bryodin 1 operatively linked with appropriate transcriptional control sequences and transformed host cells.

Furthermore, the invention relates to methods of producing bryodin 1 by recombinant means. The recombinantly produced protein can be bryodin 1, fragments or derivatives of bryodin 1 having ribosome-inactivating activity and as fusion proteins. Fusion proteins can comprise a ligand specific for a particular cell type and a functional portion of bryodin 1 which are capable of specifically directing the bryodin 1 to the cell target.

BRIEF DESCRIPTION OF THE DRAWINGS

FIG. 5 is the DNA sequence encoding bryodin 1. The sequence is numbered starting with the 5' non-coding sequences from residues 1–290 and nucleotides 1–1094. Nucleotides 914–916 represent the stop codon and 917–1094 are 3' non-coding sequences. The two underlined hexanucleotide sequences in the 3' non-coding region correspond to polyadenylation signal found in two individual clones. The arrow at amino acid 24 corresponds to the start of the mature BD1 amino terminus. The arrows at amino acid residues 271 and 290 correspond to two forms of BD1 (F2 and F1, respectively), encoding the putative mature protein (F2) and the entire pro-protein (F1).

FIGS. 6A and 6B are schematic diagrams of BD1 expression plasmids pSE13.0 and pSE 14.0.

DETAILED DESCRIPTION OF THE SPECIFIC EMBODIMENTS

Figure 1:
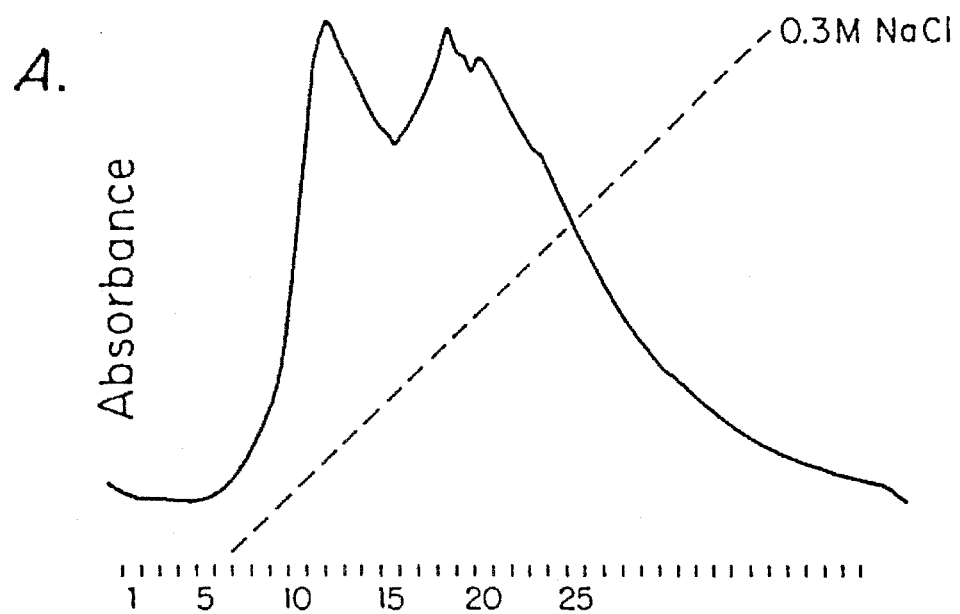
FIG. 1 provides results of the absorbence reading from CM-Sepharose chromatography of protein isolated from the root of *Bryonia dioica*.

The present invention relates to a substantially purified oligonucleotide which encodes the ribosome-inactivating protein bryodin 1 isolated from the plant *Bryonia dioica* or its complement. The oligonucleotide can be a cDNA, isolated, purified genomic DNA, RNA, or antisense RNA. Plasmids and expression vectors which comprise at least an oligonucleotide which encodes bryodin 1, or biologically active fragments and derivatives thereof are also encompassed by the present invention. The oligonucleotide is operatively linked to a transcriptional and translational control sequence in the expression vectors of the present invention. Host cells transformed with the plasmids and expression vectors are also considered part of the present invention. The above compositions can be used for the recombinant expression of large amounts of bryodin 1 or biologically active fragments or derivatives by the transformed host cells.

Bryodin 1 (BD1), a ribosome-inactivating protein, is isolated from the roots of *Bryonia dioica*. BD1 exhibits toxicity to cells similar to other plant ribosome-inactivating proteins, suggesting that it may be useful in the killing of cells, particularly if directed to a defined cell population by the ligand of a cell-specific molecule. Such ligands can include an antibody or a ligand of a cell-surface receptor (i.e., transferrin, heregulin, and others well known to the skilled artisan). BD1 can also be used in the construction of conjugates or fusion molecules comprising the ligand of a cell-specific molecule and the toxin which would be useful in the treatment of a disease state.

Purified bryodin 1 has been detected as a single band of approximately 29,000 dalton molecular weight under both reducing and non-reducing conditions. A complete primary structure of BD1 described herein has been determined by cDNA cloning and determination of a putative amino acid sequence. Sequence analysis revealed that BD1 is a type I ribosome-inactivating protein having some similarity with, but distinct from, other ribosome-inactivating proteins of the Cucurbitaceae family including trichosanthin and α-momorcharin (Montecucchi et al., 1989, *Int. J. Peptide Protein Res.* 33:263–267). All of these proteins display certain common properties characteristic of type I ribosomeinactivating proteins, such as being comprised of a single-peptide chain, a molecular weight of between 25 and 30 kDa and having an isoelectric point of approximately 9.0–10.0 (Stirpe and Barbieri, 1986, *FEBS Lett.* 196:1–8; Jimenez and Vasquez, D., 1985, *Ann. Rev. Microbiol.* 39:649–672).

BD1 can be produced by recombinant DNA techniques or chemical synthetic methods. To produce BD1 by recombinant methods, messenger RNA (mRNA) for the preparation of complementary DNA (cDNA) can be obtained from cell sources that produce BD1, whereas genomic sequences for BD1 can be obtained from any cells of *Bryonia dioica* regardless of tissue type. For example, roots of *B. dioica* can be utilized either as the source of the coding sequences for BD1 and/or to prepare cDNA or genomic libraries. Genetically-engineered microorganisms or cell lines transformed or transfected with total DNA or RNA from a source line can be used as a convenient source of DNA for screening.

Either cDNA or genomic libraries can be prepared from DNA fragments generated using techniques well known in the art. The fragments which encode BD1 can be identified by screening the prepared libraries with a nucleotide probe which would encode an amino acid sequence homologous to a portion of the N-terminal BD1 amino acid sequence (Sec. ID#2). Although portions of the coding sequence may be utilized for cloning and expression, full length clones, i.e., those containing the entire coding region for BD1, may be preferable for expression. To these ends, techniques well known to those skilled in the art for the isolation of DNA, generation of appropriate fragments, by various methods, construction of clones and libraries, and screening recombinants can be used. See, for example, the techniques described in Sambrook et al., 1989, *Molecular Cloning, A Laboratory Manual*, 2nd Ed., Cold Spring Harbor Laboratory, N.Y.

Due to the degeneracy of the nucleotide coding sequences, alternative DNA sequences which encode analogous amino acid sequences for a BD1 gene can be used in the practice of the present invention for the cloning and expression of BD1. Such alterations include deletions, additions or substitutions of different nucleotide residues resulting in a sequence that encodes the same or a functionally equivalent gene product. The gene product may contain deletions, additions or substitutions of amino acid residues within the sequence, which result in a silent change thus producing a bioactive product. Bioactivity in this context is measured by the ability of the gene product to inhibit protein synthesis.

Any amino acid substitutions can be made on the basis of similarity in polarity, charge, solubility, hydrophobicity/hydrophilicity and/or the amphipathic nature of the residue involved. For example, negatively charged amino acids include aspartic and glutamic acid; positively charged amino acids include lysine and arginine; amino acids with uncharged polar head groups having similar hydrophilicity values include the following: leucine, isoleucine, valine; glycine, alanine; asparagine, glutamine; serine, threonine; phenylalanine, tyrosine.

In order to express a biologically active bryodin 1, the nucleotide sequence encoding BD1, or a functionally equivalent nucleotide sequence, is inserted into an appropriate vector, i.e., a vector which contains the necessary elements for the transcription and translation of the inserted coding sequence. Modified versions of the BD1 sequence can be engineered to enhance stability, production, purification, yield or toxicity of the expressed product. For example, the expression of a fusion protein or a cleavable fusion protein comprising BD1 and a heterologous protein can be engineered. Such a fusion protein can be designed so that the fusion protein can be readily isolated by affinity chromatography; e.g., by immobilization on a column specific for the heterologous protein. Where a cleavage site is engineered between the BD1 moiety and the heterologous protein, the BD1 protein can be released from the chromatographic column by treatment with an appropriate enzyme or agent that disrupts the cleavage site (e.g., see Booth et al., 1988, *Immunol. Lett.* 19:65–70; and Gardella et al., 1990, *J. Biol. Chem.* 265:15854–15859).

Methods which are well known to those skilled in the art can be used to construct expression vectors containing a BD1 coding sequence and appropriate transcriptional/translational control signals. These methods include in vitro recombinant DNA techniques, synthetic techniques and in vivo recombination/genetic techniques. See, for example, the techniques described in Sambrook et al., 1989, *Molecular Cloning: A Laboratory Manual*, 2nd Ed., Cold Spring Harbor Laboratory, N.Y.

A variety of host-expression systems can be utilized to express the BD1 coding sequence. These include, but are not limited to, microorganisms, such as bacteria transformed with a recombinant bacteriophage DNA, plasmid DNA or cosmid DNA expression vector containing the BD1 coding sequence; yeast transformed with recombinant yeast expression vectors containing the BD1 coding sequence; plant cell systems infected with recombinant virus expression vectors (e.g., cauliflower mosaic virus, CaMV; tobacco mosaic virus, TMV) or transformed with recombinant plasmid expression vectors, such as Ti plasmid, containing the BD1 coding sequence. To use mammalian expression systems, the BD1 ribosome-inactivating activity would have to be blocked or masked until lysis of the host cell or secretion of BD1 into the culture medium to protect the host cell from the toxin effects of BD1 or a mutant host cell resistant to the bryodin must be used.

Depending on the host/vector system utilized, any of a number of suitable transcription and translation elements including constitutive and inducible promoters, transcription enhancer elements, transcription terminators, etc., can be used in the expression vector (see, e.g., Bitter et al., 1987, *Methods in Enzymol.* 153:516–544). For example, when cloning in bacterial systems, inducible promoters such as pL of bacteriophage λ; plac, ptrp, ptac (ptrp-lac hybrid promoter) and the like may be used. Promoters produced by recombinant DNA or synthetic techniques can also be used to provide for controlled and high level transcription of the inserted BD1 coding sequence.

In bacterial systems, a number of expression vectors can be advantageously selected depending upon the use intended for the BD1 expressed. For example, when large quantities of BD1 are desired, vectors which direct the expression of high levels of protein product, possibly as a fusion with a hydrophobic signal sequence, which directs the expressed product into the periplasm of the bacteria or the culture medium where the protein product is readily purified may be desired. Certain fusion protein engineered with a specific cleavage site to aid in recovery of the BD1 may also be desirable. Such vectors adaptable to such manipulation include, but are not limited to, the pET series of *E. coli* expression vectors (Studier et al., 1990, *Methods in Enzymol.* 185:60–89).

In yeast, a number of vectors containing constitutive or inducible promoters can be used. For a review, see *Current Protocols in Molecular Biology*, Vol. 2, 1988, ed. Ausubel et al., Greene Publish. Assoc. & Wiley Interscience, ch. 13; Grant et al., 1987, "Expression and Secretion Vectors for Yeast," in *Methods in Enzymol.* 153:516–544; Glover, 1986, DNA Cloning, Vol. II, IRL Press, Wash., D.C., Ch. 3; and Bitter, 1987, "Heterologous Gene Expression in Yeast," in *Methods in Enzymol.* 152:673–684. A constitutive yeast promoter such as ADH or Leu2 or an inducible promoter such as GAL can be used ("Cloning in Yeast," ch. 3, R. Rothstein In: *DNA Cloning*, Vol. 11, A Practical Approach, Ed. D. M. Glover, 1986, IRL Press, Wash. D.C.). Alternatively, vectors can be used which promote integration of foreign DNA sequences into the yeast chromosome.

In cases where plant expression vectors are used, the expression of the BD1 coding sequence can be driven by a number of promoters. For example, viral promoters such as the 35S RNA and 19S RNA promoters of CaMV (Brisson et al., 1984, *Nature* 310:511–514), or the coat protein promoter to TMV (Takamatsu et al., 1987, *EMBO J.* 6:307–311) can be used. Alternatively, plant promoters such as the small subunit of RUBISCO (Coruzzi et al., 1984, *EMBO J.* 3:1671–1680; Brogli et al., 1984, *Science* 224:838–843); or heat shock promoters, e.g., soybean hsp17.5-E or hsp17.3-B (Gurley et al., 1986, *Mol. Cell. Biol.* 6:559–565) can be used. These constructs can be introduced into plant cells using Ti plasmid, Ri plasmid, plant viral vectors, direct DNA transformation, microinjection, electroporation and other techniques well known to the skilled artisan. See, for example, Weissbach & Weissbach, 1988, *Methods for Plant Molecular Biology*, Academic Press, New York, Section VIII, pp 421–463; and Guerson & Corey, 1988, *Plant Molecular Biology*, 2d ed., Blackie, London, Ch. 7–9.

Other expression systems such as insects and mammalian host cell systems are well known in the art, but would have to be modified or adapted to produce a toxic molecule. One potential approach to modification would be to isolate mutant insect or mammalian cell lines resistant to BD1, as mentioned above.

In addition to producing bryodin 1 by recombinant DNA techniques, BD1 can also be produced in whole or in part by solid phase chemical synthetic techniques based on the determined amino acid sequence (see, Creighton, 1983, *Protein Structures and Molecular Principles*, W. H. Freeman and Co., New York, pp. 50–60; Stewart and Young, 1984, *Peptide Synthesis*, 2d Ed., Pierce Chemical Co.). This approach may be particularly useful in generating segments or fragments of BD1 corresponding to one or more of its biologically active regions.

In another aspect of the present invention, the expressed recombinant bryodin 1, or a functional equivalent, can be used with a ligand for a cell surface receptor to target the toxin to a specific cell population as a toxin-ligand conjugate.

The skilled artisan understands the term "ligand" includes within its scope any molecule that specifically binds or reactively associates or complexes with a receptor or other receptive moiety associated with a given target cell population. This cell-reactive molecule, or ligand, to which the toxin is linked via a linker in the conjugate, can be any molecule that binds to, complexes with or reacts with the cell population sought to be therapeutically or otherwise biologically affected. The cell-reactive molecule acts to deliver the toxin to the particular target cell population with which the ligand reacts. Such molecules include, but are not limited to, large molecular weight proteins (generally greater than 10,000 daltons) such as, for example, antibodies or adhesion molecules, smaller molecular weight proteins (generally, less than 10,000 daltons), polypeptides, or peptide ligands, and non-peptidyl ligands.

The non-immunoreactive protein, polypeptide, or peptide ligands which can be of use to form the conjugates of the present invention may include, but are not limited to, transferrin, epidermal growth factors, bombesin, gastrin, gastrin-releasing peptide, platelet-derived growth factor, IL-2, IL-6, or tumor growth factors, such as TGF-α and TGF-β. Non-peptidyl ligands may include, for example, steroids, carbohydrates and lectins.

The immunoreactive ligands comprise an antigen-recognizing immunoglobulin (or antibody), or antigen-recognizing fragment thereof. Particularly preferred immunoglobulins are those immunoglobulins which can recognize a tumor-associated antigen capable of internalization. As used, "immunoglobulin" may refer to any recognized class or subclass of immunoglobulin such as IgG, IgA, IgM, IgD or IgE. Preferred are those immunoglobulins which are within the IgG class of immunoglobulins. The immunoglobulin can be derived from any species. Preferably, however, the immunoglobulin is one of human or murine origin. Further, the immunoglobulin may be polyclonal or monoclonal, preferably monoclonal.

As noted, one skilled in the art will appreciate that the invention also encompasses the use of antigen recognizing immunoglobulin fragments. Such immunoglobulin fragments include, for example, the Fab', F(ab')$_2$, Fv or Fab fragments, or other antigen recognizing immunoglobulin fragments. Such immunoglobulin fragments can be prepared, for example, by proteolytic enzyme digestion, for example, by pepsin or papain digestion, reductive alkylation, or recombinant techniques. The materials and methods for preparing immunoglobulin fragments are well known to those skilled in the art. See generally, Parham, 1983, *J. Immunol.* 131:2895; Lamoye et al., 1983, *J. Immunol. Methods* 56:235; Parham, 1982, *J. Immunol. Methods* 53:133 and Matthew et al., 1982, *J. Immunol. Methods* 50:239.

The immunoglobulin can also be "chimeric" as that term is recognized in the art. Also, the immunoglobulin can be a "bifunctional" or "hybrid" antibody, that is, an antibody which may have one "arm" having a specificity for one antigenic site, such as a tumor-associated antigen, while the other arm recognizes a different target, for example, a second cell type-specific receptor molecule. In any case, the hybrid antibodies have a dual specificity, preferably with one or more binding sites specific for a target antigen, for example, an antigen associated with a tumor, an infectious organism, or other disease state.

Bifunctional antibodies are described, for example, in European Patent Publication EPA 0 105 360. Such hybrid or bifunctional antibodies may be derived, as noted, either biologically by cell fusion techniques, or chemically, especially with cross-linking agents or disulfide bridge-forming reagents, and may be comprised of whole antibodies and/or fragments thereof. Methods for obtaining such hybrid antibodies are disclosed, for example, in PCT application WO83/03699, published Oct. 27, 1983, and European Patent Publication, EPA 0 217 577, published Apr. 8, 1987, both of which are incorporated herein by reference.

In addition, the immunoglobulin may be a single chain antibody ("SCA"). These can consist of single chain Fv fragments ("scFv") (Ward et al., 1989, *Nature* 341:544) in which the variable light ("$V_L$") and variable heavy ("$V_H$") domains are linked by a peptide bridge or by disulfide bonds. Also, the immunoglobulin may consist of single $V_H$ domains (dAbs) which possess antigen-binding activity. See, e.g., Winter and Milstein, 1991, *Nature* 349:295 and Glockshaber et al., 1990, *Biochemistry* 29:1362. Additionally, the immunoglobulin may consist of disulfide-stabilized Fvs (Brinkman et al., 1993, *Proc. Natl. Acad Sci.* 90:7538.

A preferred embodiment of an immunological ligand as part of a ligand/toxin conjugate for use in the present invention is a chimeric monoclonal antibody, preferably those chimeric antibodies which have a specificity toward a tumor-associated antigen. As used herein, the term "chimeric antibody" refers to a monoclonal antibody comprising a variable region, i.e., binding region, from one source or species and at least a portion of a constant region derived from a different source or species, usually prepared by recombinant DNA techniques. Chimeric antibodies comprising a murine variable region and a human constant region are especially preferred in certain applications of the present invention, particularly human therapy. Such murine/human chimeric antibodies are the product of expressed immunoglobulin genes comprising DNA segments encoding murine immunoglobulin variable regions and DNA segments encoding human immunoglobulin constant regions. Other forms of "chimeric antibodies" encompassed by the present invention are those in which the class or subclass has been modified or changed from that of the original antibody. Such "chimeric" antibodies are also referred to as "class-switched antibodies." Methods for producing chimeric antibodies involve conventional recombinant DNA and gene transfection techniques now well known in the art. See, e.g., Morrison et al., 1984, *Proc. Natl. Acad. Sci. USA* 81:6851; U.S. Pat. No. 5,202,238, and U.S. Pat. No. 5,204,244.

Encompassed by the term "chimeric antibody" is the concept of "humanized antibody," that is, those antibodies in which the framework or "complementarity determining regions" (CDR) have been modified to comprise the CDR of an immunoglobulin of different specificity as compared to that of the parent immunoglobulin. In a preferred embodiment, a murine CDR is grafted into the framework region of a human antibody to prepare the "humanized antibody." See, e.g., Riechmann et al., 1988, *Nature* 332:323; and Neuberer et al., 1985, *Nature* 314:268. Particularly preferred CDRs correspond to those representing sequences recognizing the antigens noted above for chimeric and bifunctional antibodies.

One skilled in the art will recognize that a bifunctional chimeric antibody can be prepared which would have the benefits of lower immunogenicity of the chimeric or humanized antibody, as well as the flexibility, especially for therapeutic uses, of the bifunctional antibody described above. Such bifunctional-chimeric antibodies can be synthesized, for instance, by chemical synthesis using cross-linking agents and/or recombinant methods of the type described above. In any event, the present invention should not be construed as limited in scope by any particular method of production of an antibody whether bifunctional, chimeric, bifunctional-chimeric, humanized or an antigen-recognizing fragment or derivative thereof.

Further, as noted above, the immunoglobulin, or fragment thereof, used in the present invention may be polyclonal or monoclonal in nature. Monoclonal antibodies are the preferred immunoglobulins, however. The preparation of such polyclonal or monoclonal antibodies now is well know to those skilled in the art who are fully capable of producing useful immunoglobulins which can be used in the present invention. See, e.g., Kohler and Milstein, 1975, *Nature* 256:495. In addition, hybridomas and/or monoclonal antibodies which are produced by such hybridomas and which are useful in the practice of the present invention are publicly available from such sources as the American Type Culture Collection (ATCC), 12301 Parklawn Drive, Rockville, Md. 20852, or commercially, for example, from Boehringer-Mannheim Biochemicals, P.O. Box 50816, Indianapolis, Ind. 46250.

A particularly preferred monoclonal antibody of the present invention is one that binds a tumor-associated cell surface antigen and is capable of internalization. In a particular embodiment of the present invention, the toxin is conjugated to the chimeric antibody BR96 ("chiBR96"), disclosed in U.S. Ser. No. 07/544,246, filed Jun. 26, 1990, and which is equivalent to PCT Published Application, WO91/00295, published Jan. 10, 1991. ChiBR96 is an internalizing murine/human chimeric antibody and is reactive with a fucosylated Lewis Y antigen expressed by human carcinoma cells, such as those derived from the breast, lung, colon, and ovarian carcinomas. The hybridoma expressing chimeric BR96 and identified as the chiBR96 was deposited on May 23, 1990 under the terms of the Budapest Treaty, with the American Type Culture Collection, and designated ATCC HB 10460.

One of the preferred methods of making an immunotoxin of the present invention is by chemically conjugating the recombinant bryodin 1 toxin of the present invention with the ligand, preferably a monoclonal antibody or a fragment thereof, as described above. Many methods of chemical conjugation are well known to the skilled artisan. See, e.g., Vitetta et al., 1987, *Science* 238:1098; Pastan et al., 1986, *Cell* 47:641; and Thorpe et al., 1987, *Cancer Res.* 47:5924). These methods generally conjugate the toxin and the antibody by means of cross-linking agents that introduce a disulfide bond between the two proteins. Immunotoxins which have been prepared with nonreducible linkages have been shown to be consistently less cytotoxic than similar toxins cross-linked by disulfide bonds.

One preferred method uses N-succinimidyl-3-(2-pyridyldithio)-propionate (SPDP) and 2-iminothiolane hydrochloride (2IT). Other preferred reagents are sodium S-4-succinimidyloxycarbonyl-α-methyl benzyl thiosulfate (SMBT) and 2IT or succinimidyloxy carbonyl-α-methyl-α(2-pyridyldithio)-toluene and 2IT. Each group of reagents introduces a disulfide bond between the toxin and the antibody which is reducible, but the bond is also resistant to breakdown providing stability of the conjugate in vitro and in vivo. Upon internalization into lysosomes or endosomes by the target cell, the bond is reduced and the toxin enters the cytoplasm, binds elongation factor 2, disrupting protein synthesis.

Another preferred embodiment of the present invention is recombinant immunotoxins, particularly single-chain immunotoxins. These molecules have the advantage over toxin-antibody conjugates (immunotoxins) in that they are more readily produced than the conjugates, and homogeneous populations of toxin molecules are generated, i.e., single peptide composed of the same amino acid residues.

The techniques for cloning and expressing DNA sequences encoding the amino acid sequences corresponding to a single chain derivative of a parental antibody are well known to the skilled artisan, as discussed above. The nucleotide sequence of bryodin 1 is provided by the present invention and various methods of constructing recombinant toxin fusion proteins are described in Pastan and Fitzgerald, 1991, *Science* 254, 1173; Siegall et al., 1988, *Proc. Natl. Acad. Sci. USA* 85:9738; Batra et al., 1991, *Mol. Cell Biol.* 11:2200; O'Hare et al., 1990, *FEBS Lett.* 273:200; Westby et al., 1992, *Bioconj. Chem.* 3:375.

The recombinant ribosome-inactivating toxin, bryodin 1, of the present invention is useful for therapeutic applications, both in vitro and in vivo in its isolated form and as ligand-toxin conjugates and recombinant toxin fusion proteins. Ribosome-inactivating proteins isolated from Cucurbitaceae plants have found use as, among others, abortifacients, immunomodulators, anti-minor and anti-viral agents (Ng et al., 1992, *Gen. Pharmac.* 13:575–590) or as an anti-malarial agent (Amorim et al., 1991, *Mem. Inst. Oswaldo Cruz* 86:177).

Recombinant bryodin 1 is particularly useful as a ligand-toxin conjugate or a recombinant toxin fusion protein since BD1 is less toxic than many other protein toxins and ribosome-inactivating proteins that have been used to construct immunotoxins and is particularly potent at inhibiting protein synthesis once inside the cell. Ligand-toxin conjugate and recombinant toxin fusion proteins can be used for either in vivo treatment of cells removed from the body or a patient to remove or kill a desired cell population prior to reinfusion of the remaining cells back into the patient or directly administering the recombinant-toxin fusion into the patient.

For ex vivo uses, cells, such as bone marrow, may be removed from a patient suffering from cancer and the marrow purged by treatment with the ligand-toxin conjugate or fusion protein. Following treatment, the marrow is infused back into the patient (see, e.g., Ramsay et al., 1988, *J. Clin. Immunol.* 8:81–88).

For in vivo uses, the present invention provides a method for selectively killing cells, i.e., tumor cells, expressing the antigen that specifically binds the ligand, or functional equivalent of the ligand-toxin conjugate or fusion molecule. This method comprises reacting the recombinant toxin conjugate or fusion molecule with the tumor cell by administering to a subject a pharmaceutically effective amount of a composition containing at least one ligand-recombinant toxin conjugate or fusion molecule of the present invention.

In accordance with the present invention, the subject may be human, equine, porcine, bovine, murine, canine, feline, and avian. Other warm blooded animals are also included within the scope of the present invention.

The claimed invention also provides a method of inhibiting the proliferation of mammalian tumor cells. This method comprises contacting the mammalian tumor cells with a proliferation inhibiting amount (i.e., effective amount) of a tumor targeted recombinant toxin joined to a ligand specific for a tumor-associated antigen so as to inhibit proliferation of the mammalian tumor cells.

The following examples are presented to illustrate the present invention and to assist one of ordinary skill in making and using the same. The examples are not intended in any way to otherwise limit the scope of the invention.

EXAMPLE 1

Purification of Bryodin 1 from *Bryonia dioica*

This example describes the preparation of total protein from the root of *Bryonia dioica* and the separation of the ribosome-inactivating proteins, including the novel protein bryodin 1.

*Bryonia dioica* roots (Poyntzfield Herb Nursery, Ross-shire, Scotland) were cleaned, peeled, shred and homogenized using a Waring blender in phosphate-buffered saline (PBS, 1 liter PBS:550 g root material). The slurry obtained was stirred for 16 hours at 4° C. and strained through cheesecloth. After removal of the plant material, the filtrate was centrifuged at 15×g for 15 minutes at 4° C. to remove large particles and then centrifuged a second time at 50×g for 20 minutes to clarify. The supernatant was then filtered through a sterile 0.22 micron filter and dialyzed versus 5 mM sodium phosphate buffer, pH 6.5.

Figure 2:
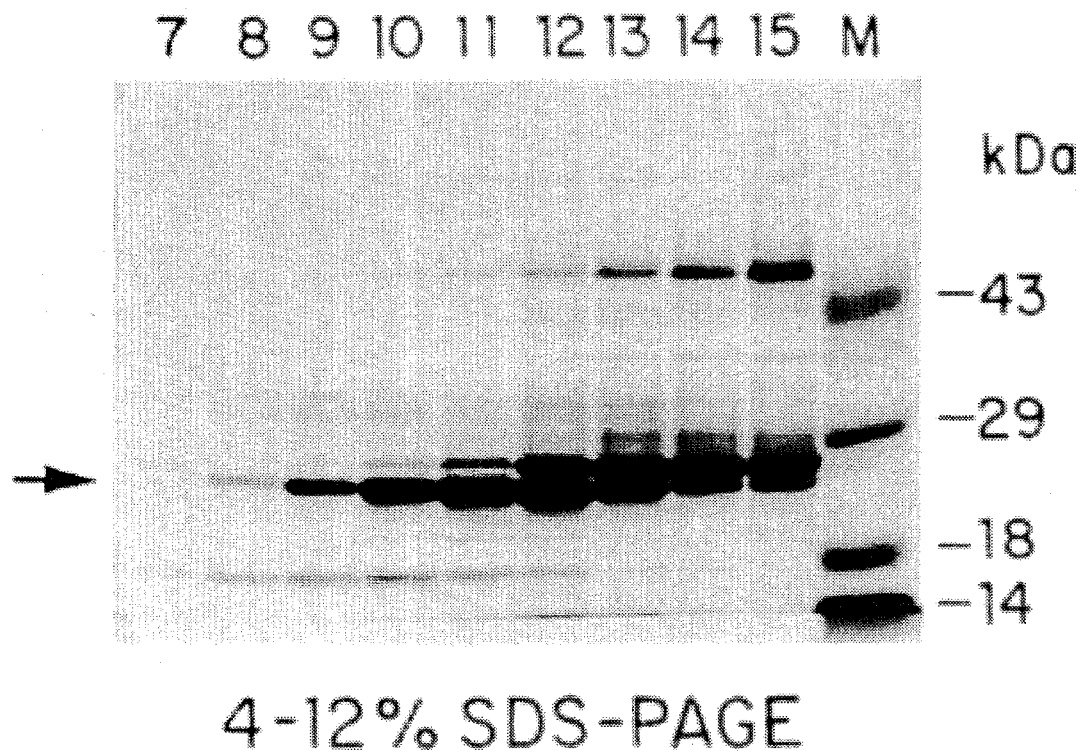
FIG. 2 is the result of SDS-PAGE analysis of fractions 9 through 15 from the CM-Sepharose chromatography separation. Lane M contains molecular weight standards: ovalbumin (43,000 mw), carbonic anhydrase (29,000 mw), β-lactoglobulin (18,000 mw), lysozyme (14,000 mw), bovine trypsin inhibitor (6,000 mw), and insulin (2,000 mw).

Plant proteins were then separated on the basis of their charge and size using a five-step procedure. First, the dialyzed root extract was applied to a CM-Sepharose column (Pharmacia, Uppsala, Sweden), equilibrated to 5 mM sodium phosphate pH 6.5. Proteins were eluted from the column using a salt gradient of 0 to 0.3M NaCl. Second, 4 ml fractions were collected and the optical density of the effluent was monitored at 280 nm (FIG. 1). The chromatography fractions were then evaluated by electrophoresis. Fifteen μl aliquots of each collected fraction were added to SDS-PAGE sample buffer, boiled at 100° C. for 5 min. and separated on 4–12% SDS-PAGE gradient gels (Laemmili, 1970, *Nature* 227:680–685). The gels were then stained with Coomassie blue to resolve the separated proteins (FIG. 2).

Figure 3:
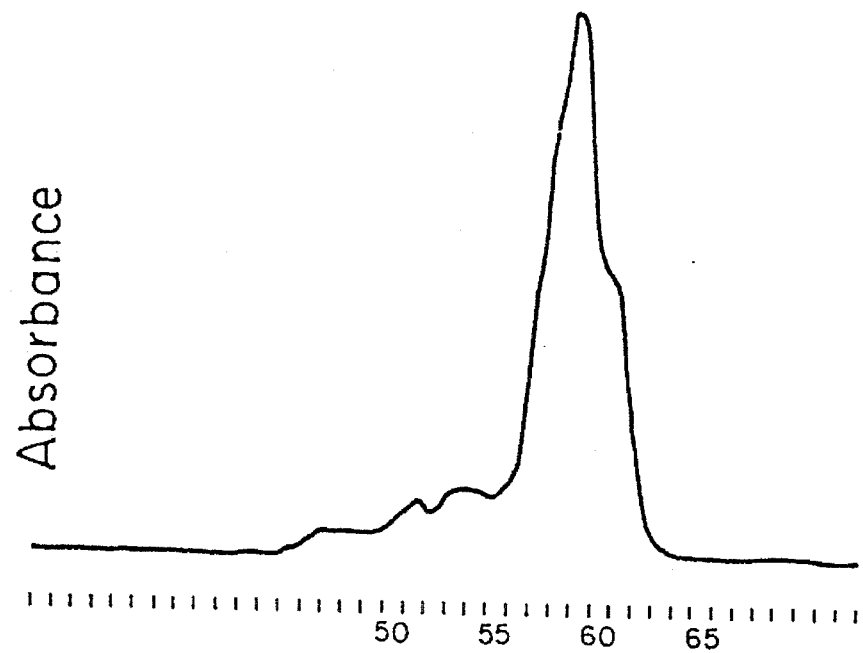
FIG. 3 is a chromatogram obtained from a TSK-3000 size exclusion column. Fractions containing the 29 kDa band were pooled from the CM-Sepharose chromatography separation and concentrated to less than 8 ml. The concentrate was applied to the column and absorbence monitored at 280 nm.
Figure 4:
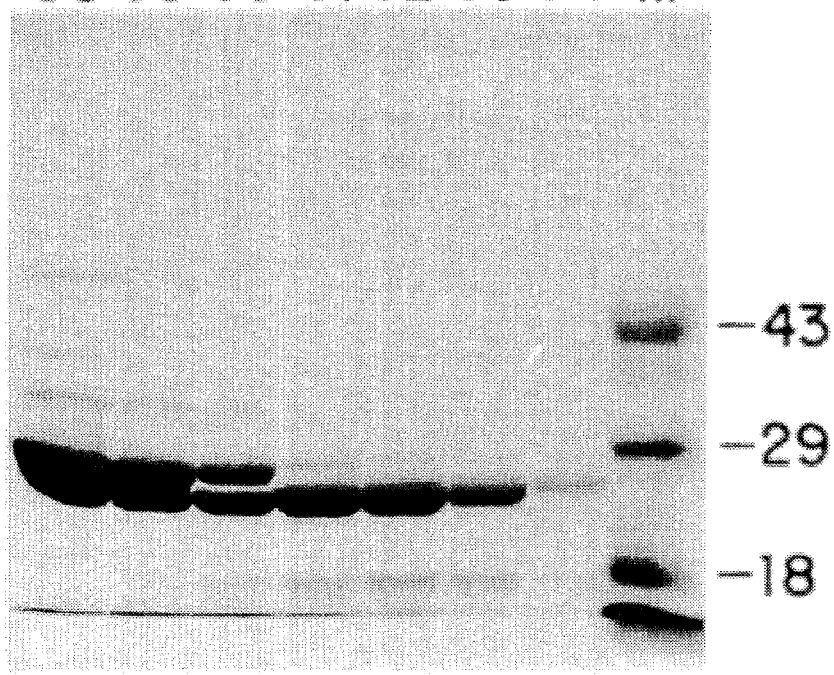
FIG. 4 illustrates the result obtained for SDS-PAGE analysis of fractions 58 through 64 from size exclusion chromatography of the partially purified bryodin. Lane M contains molecular weight standards: ovalbumin (43,000 mw), carbonic anhydrase (29,000 mw), and β-lactoglobulin (18,000 mw).

In the third step of the purification, fractions 9 through 15 which contained a 29 kDa protein band were pooled and then concentrated to a volume of less than 8 ml using a Centriprep 10 (Areicon, Bedford, Mass.). The fourth step was to apply the concentrate to a size-exclusion column TSK-3000 (TosoHaas, Inc., Philadelphia, Pa.) and then to elute the plant proteins isocratically. Three ml fractions were collected and the eluate was monitored at 280 nm (FIG. 3). Following size-exclusion chromatography, the fifth step in the purification process was to analyze the fractions by SDS-PAGE as described above, except that a 12% SDS-PAGE gel was used. Proteins were resolved by Coomassie blue staining. Two discrete protein bands migrating at 29 kDa and 27 kDa were observed in the peak fractions 58 through 64 (FIG. 4). These fractions were pooled separately and this material was used for further characterization.

EXAMPLE 2

N-Terminal Amino Acid Sequence Analysis of Bryodin

In this example, the N-terminal amino acid sequence of the 29 kDa proteins contained in the pooled fractions was determined. The first 32 amino acid residues of the 29 kDa protein band was unambiguously determined and was found to be identical to the bryodin (bryodin 1) described by Stirpe.

N-terminal amino acid sequence was determined by using the following methods which are briefly described. The protein band was individually recovered from SDS-polyacrylamide gels by electroblotting onto a Problott membrane (Applied Biosystems, Foster City, Calif.) using a Mini-transblot Electrophoretic Transfer Cell (Bio Rad Laboratories, Richmond, Calif.) (Matsudaira, 1987, *J. Biol. Chem.* 262: 10035–10038). The membrane was stained with Coomassie brilliant blue, then destained, and the 29-kDa band was excised for subsequent amino terminal sequence analysis.

The sample was sequenced in a pulsed liquid phase protein sequencer (Model 476A, Applied Biosystems) equipped with a vertical cross-flow reaction cartridge using manufacturer's released cycle programs. Phenylthiohydantoin amino acid derivatives were analyzed by reversed-phase HPLC with a PTH C 18 column (Applied Biosystems) using sodium acetate/tetrahydrofuran/acetonitrile gradient for elution (Tempst and Reviere, 1989, *Anal. Biochem.* 183:290–300). Data reduction and quantitation were performed using a Model 610A chromatogram analysis software (Applied Biosystems).

The amino-terminal amino acid sequence of BD1 was performed with 47 pmoles (based on the initial yield of identified Val-1), electroblotted onto Problott membrane. A single amino acid sequence was obtained and unambiguous identification of PTH-amino acid derivatives was possible up to residue 32 (Seq. I.D. #1).

EXAMPLE 3 cDNA Cloning of Bryodin 1

In this example, total RNA from Bryonia dioica leaf was used for the cDNA cloning of Bryodin 1. Briefly, total RNA was extracted from 2.1 g of leaf material using TRI reagent (Molecular Research Center, Inc., Cincinnati, Ohio) as per manufacturer's protocol. Frozen leaves were pulverized, solubilized in TRI reagent and homogenized. The RNA was extracted with chloroform, precipitated with isopropanol and washed in ethanol. The resulting total RNA was resuspended in $H_2O$, quantitated and analyzed by electrophoresis in formaldehyde-agarose gels and visualized by staining with ethidium bromide. Approximate yield was 0.9 mg total RNA/g of leaf material.

Oligo (dT)-primed cDNA (using total RNA as template) was amplified by PCR using degenerate oligonucleotide mixtures, BD1-p20 (Seq. ID#3) and BD1-p22 (Seq. ID#4), to isolate exact BD1 sequence between amino acids 7 and 30. The products of the PCR reaction were subcloned into the vector pCRII (Invitrogen Corp., San Diego, Calif.), as per manufacturer's protocol using the TA cloning kit. Briefly, the PCR amplified products containing 3' single deoxyadenosines were ligated into the pCRII vector prepared with 3'dT overhangs at the EcoRI site. The ligation product was transformed into DHS5α *E. coli* cells (Sambrook et al., 1989, *Molecular Cloning, A Laboratory Manual,* 2nd Ed., Cold Spring Harbor Laboratory, N.Y.).

Recombinant clones were selected for DNA sequence analysis based on the presence of 100–120 base pair (bp) inserts, as determined by agarose gel electrophoresis (Sambrook et al., supra). DNA sequencing (Sanger et al., 1977, *Proc. Nat'l. Acad. Sci.* 74, 5463) was performed by dideoxynucleotide termination using Sequenase (United States Biochemical Corp., Cleveland, Ohio). One clone containing the correct nucleotide match to the amino-terminal sequence of BD1 was identified following sequence analysis of 81 individual clones.

The 3' end of the BD1 gene was amplified by 3' RACE as follows: following first strand cDNA amplification of total RNA with oligonucleotide XSC-T17 (Seq. ID#9) and-XSC (Seq. ID#10), and cloned into pCRII is described above. Clones containing BD1 sequences were selected by hybridization on nylon filters probed with [$^{32}$P]-labeled BD1-Ex4 (Seq. ID#6), an oligonucleotide having the exact nucleotide sequence of the region of the BD1 gene located downstream of the PCR primer BD1-Ex2. Two clones were identified by DNA sequencing that encoded the BD1 gene open reading frame.

To identify the exact 5' end of the BD1 gene, 5' RACE was performed using the 5' RACE System (Gibco BP, L, Gaithersburg, Md.) as per manufacturer's protocol. Briefly, first strand cDNA was synthesized using the oligonucleotide primer BD1-Full (Seq. ID#7), tailed with dCTP, and the resultant first strand was PCR amplified with oligonucleotide primers BD1-p2 (Seq. ID#8, encoding amino acid residues 26–36) and AP (Seq. ID#11, encoding poly-G adaptor primer that binds to the poly-C tail). The resulting amplified DNA fragments were subcloned into plasmid pCRII as described above. BD1 encoding clones were selected by hybridization on nylon filters probed with [$^{32}$P]-labeled BD1-Ex2 (Seq. ID#5). Two positive clones were selected which contained cDNA encoding BD1, pCRII BD1 c1.1 and pCRII BD1 c1.6 for DNA sequencing. The complete DNA sequence encoding BD1 is shown in FIG. 5.

The oligonucleotides used in the cDNA cloning BD1 were as follows, with sequences in brackets denoting nucleotide degeneracy and the sequences in parentheses denoting the corresponding amino acid sequence.

| | | |
|---|---|---|
| BD1-20 | 5'-CCTAGCCCATGGATGT[TG]AGCTT[CT]CGTTT-3'<br>(residues 1–6: AspValSerPheArgLeu); | (Seq. ID #3); |
| BD1-22 | 5'-CCTAGCGAATTCCTA[CG]AGAGG[GT]AT[GA]TTGTA[GC]AC-3'<br>(residues 31–36: ValTyrAsnIleProLeu); | (Seq. I.D. #4); |
| BD1-Ex2 | 5'-TTATCAGGTGCTACAACCACATCC-3'<br>(residues 6–13: LeuSerGlyAlaThrThrThrSer); | (Seq. ID#5); |
| BD1-Ex4 | 5'-GAAGCTCTTCCATACGAAAGG-3'<br>(residues 23–29: GluAlaLeuProTyrGluArg); | (Seq. ID#6); |
| BD1-Full | 5'-CAAAGATCCTCTGAATTCTTACTATATACCATAAAGTCCATGT<br>TCAAAGCCGATGAGTGTCATAGAAATGTCCTC-3'<br>(Residues 251–267:<br>GluAspIleSerMetThrLeuIleGlyPheGluHisGlyLeuTyrGlyIle); | (Seq. ID#7); |
| BD1-p2 | 5'-GAGAGGTATGTTGTAGACTTTCCT-3'<br>(Residues 29–36: ArgLysValTyrAsnIleProLeu); | (Seq. ID#8); |

| | | |
|---|---|---|
| XSCT17 | 5'-GACTGGAGTCGACATCGATTTTTTTTTTTTTTTTT-3' | (Seq. ID#9); |
| XSC | 5'-GACTCGAGTCGACATCG-3' | (Seq. ID#10); |
| AP | 5'-GGCCACGCGTCGACTAGTACGGGIIGGGIIGGGIIG-3' | (Seq. ID#11) |

EXAMPLE 4

Construction of Expression Plasmids and Expression of Recombinant BD1

In this example, two plasmids (pSE 14.0 and pSE 13.0) were constructed which encoded and expressed recombinant bryodin 1 (rBD1F1 and rBD1F2, respectively). Also, in this example, bryodin 1 expressed by the plasmids was purified and demonstrated to inhibit protein synthesis.

Briefly, pSE13.0 was constructed as follows. The cDNA sequence encoded by plasmid pCRII BD1 cl.1 was used to PCR-amplify a 770 bp DNA fragment with primer 1.

5'-GTCAGAGTTCCATGGATGR-GAGCTTTCGTTTATCAGGTGCTAC AACCA-CATCCTAT-3' (Seq. ID#12);
and primer 2
5'-CAAAGATCCTCTGAATTCTTATTATG-CAATATTATTTCTGTTAG CAGCAA-3' (Seq. ID#13).

The 5' PCR primer (primer 1 was designed to encode a unique NcoI restriction site adjacent to an ATG initiation codon and the first 14 codons of the BD1 gene. The 3' PCR primer (primer 2) was designed to anneal to the last 9 codons of the BD1 gene corresponding to the carboxyl terminus of the mature BD1 protein. The 3' primer also contains two consecutive stop codons followed by an EcoRI restriction site.

After PCR-amplification and digestion with NcoI and EcoRI, the 747 bp NcoI-EcoRI fragment was ligated into a 5465 bp NcoI-EcoRI vector fragment prepared from plasmid pET22b (Novagen, Madison, Wis.) which is under the transcriptional control of the T7 promoter. The product of this ligation was an intermediate vector designated pSE10.0 which contained the T7 promoter, the PelB leader sequence, and the cDNA sequence encoding BD1.

The expression vector pSE13.0, containing the cDNA sequence encoding BD1 without the PelB leader sequence was constructed by digesting expression vector pSE10.0 with the restriction enzymes XbaI and NcoI. Following digestion, the 6106 bp fragment was ligated with the oligoduplex formed by the annealing of primer 3 and primer 4.

primer 3 5'-CTAGAGAAATAATTTTGTTTAACTT-TAAGAAGGAGATAC-3' (Seq. ID#14);

primer 4 5'-CATGGTATCTCCTTCTTAAAGTTAAA-CAAATTATTT-3' (Seq. ID#15).

The plasmid pSE14.0 was constructed similarly to pSE13.0. The cDNA sequence encoded by plasmid pCRII BD cl.1.1 was PCR amplified with primer 1 (Seq. ID#12) and primer 5.
primer 5
5'-CAAAGATCCTCTGAATTCTTAC-TATATACCATAAAGTCCATGT TCAAAGCCGAT-GAGTGTCATAGAAATGTCCTC-3' (Seq. ID#16).

The 3' primer (primer 5) encodes a unique EcoRI restriction site and anneals to the last 17 codons of the BD1 gene corresponding to the carboxyl terminus of the full BD1 protein. The 3' primer also contains two stop codons prior to the EcoRI site. After PCR amplification and NcoI-EcoRI digeston, the 807-bp fragment was ligated into pET22b exactly as described for pSE13.0, resulting in the intermediate plasmid pSE11.0. The PelB leader sequence of pSE11.0 was removed exactly as described for pSE13.0 yielding the expression plasmid pSE14.0 encoding the full BD1 form (BD1F1). The expression plasmid pSE14.0 was deposited with the American Type Culture Collection, 12301 Parklawn Drive, Rockville, Md. 20852, under the terms of the Budapest Treaty May 17, 1994, and designated ATCC 69620.

Expression from each plasmid pSE14.0 and pSE13.0 was carried out in one liter cultures of E. coli BL21 (λDE3) grown in T broth supplemented with 50 µg/ml ampicillin to $A_{650}$=0.6–0.8 and the induction with IPTG (1 mM) for 1.5 hours at 37° C. Cell pellets were collected by centrifugation and were processed by one of two methods. In the first method, the cells were lysed in 10 mM Tris, pH 7.4, 100 mM KCl, 20 mM EDTA, 10 mM 2-mercaptoethanol, 0.05% NP-40 and 5 mg lysozyme/liter of culture for 30 minutes on ice. The cell suspensions were then freeze/thawed three times, sonicated and centrifuged at 15,000 RPM for 30 minutes. In the second method the cell pellet was resuspended in 20% sucrose, 30 mM Tris HCl pH 7.5 and 1 mM EDTA on ice for 10 min. and centrifuged at 8,000 RPMs for 15 minutes. The pellet was resuspended in ice cold $H_2O$ for 10 min. and centrifuged as above. The pellet (or spheroplasts) was resuspended in 50 mM Tris-HCl (pH 8.0) and 1 mM EDTA, sonicated and centrifuged at 30K for 45 minutes. Pellets collected by both methods were then dissolved in 7M guanidine HCl, 100 mM Tris, pH 7.4, and 1 mM EDTA for 1 hour, sonicated and centrifuged at 25,000 RPM for 30 minutes.

Figure 7A:
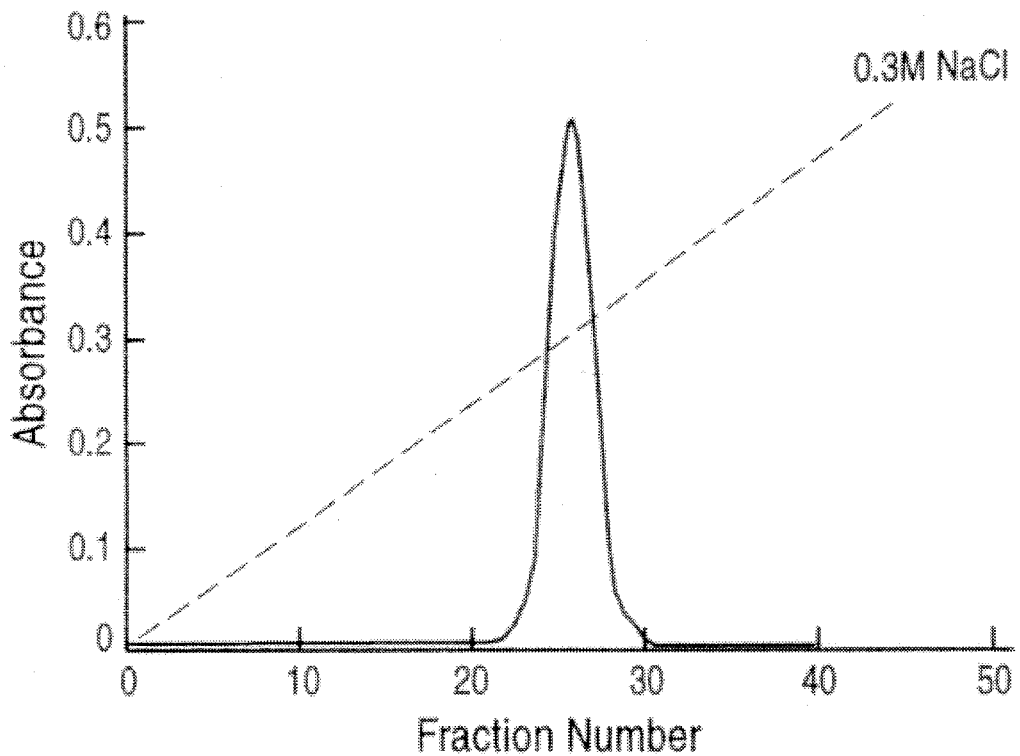
FIGS. 7A, B and C are a CM-Sepharose chromatography profile (A), SDS-PAGE with Coomassie-blue staining (B), and Western blot using anti-BD1 polyclonal antibodies (rabbit) (C) of recombinant BD1F1 (amino acid residues 24–290) which was denatured and refolded. Fractions on the chromatography profile correspond to fraction numbers on the gels. N=Native BD1.
Figures 7B, 7C:
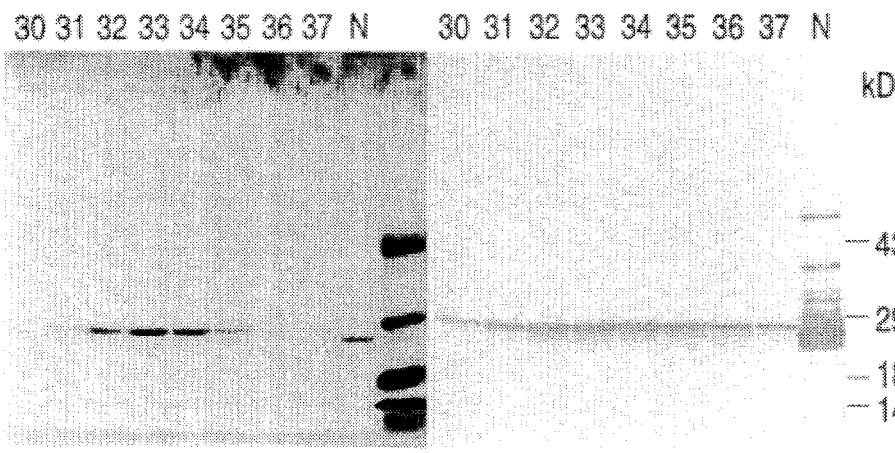
Figure 8A:
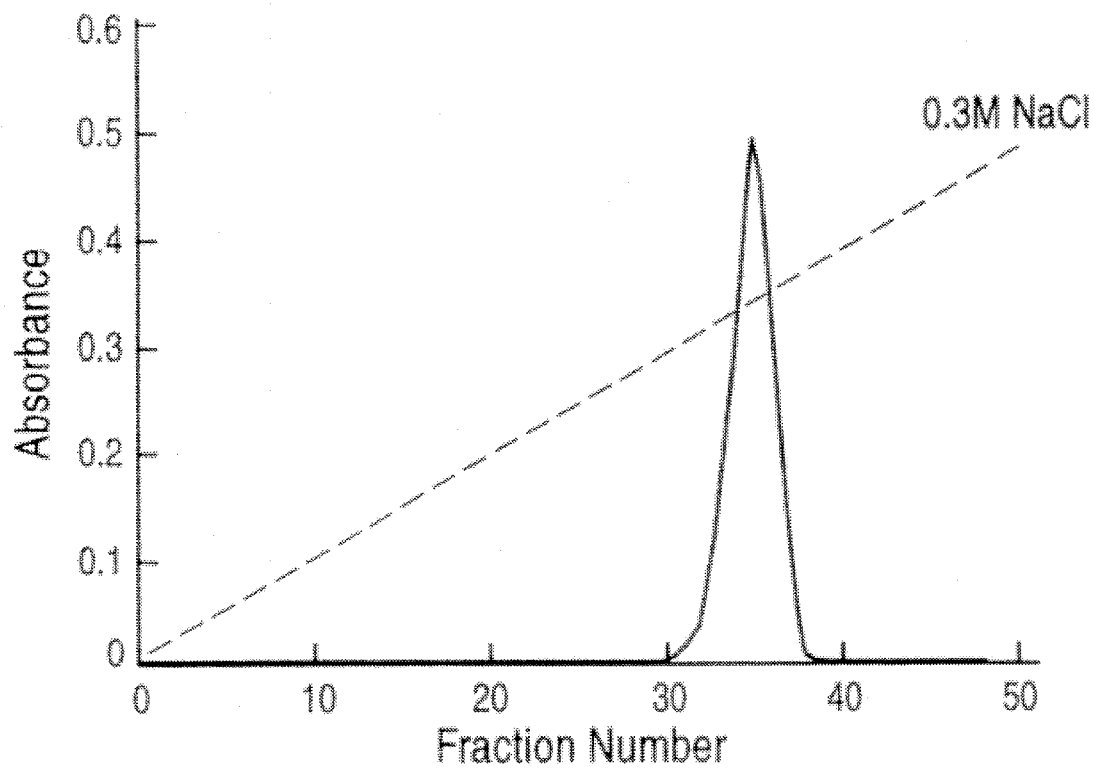
FIGS. 8A, B and C are the results of purification of recombinant BD1F2 (amino acid residues 24–270) (A); CM-Sepharose chromatography profile (B); SDS-PAGE stained with Coomassie-Blue (C); and Western blot stained with anti-BD1 polyclonal antisera. N=Native BD1.
Figures 8B, 8C:
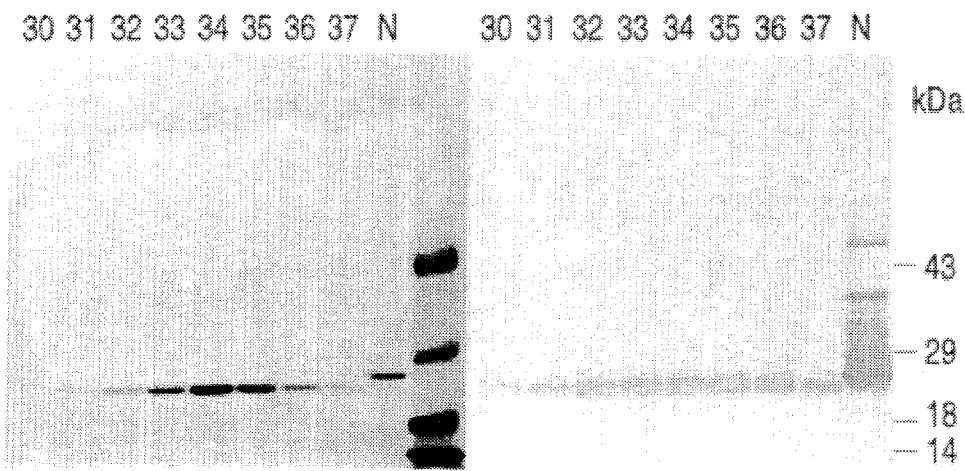

The denatured recombinant bryodin 1 (BD1) protein expressed and isolated from pSE 13.0 or pSE14.0 was refolded in 0.4M L-arginine PBS, and 70 mM guanidine HCl at a concentration of 80 µg/ml protein at 4° C. for >24 hours. The protein was extensively dialyzed against 5 mM $NaH_2PO_4$ and isolated by CM-sepharose (weak-cation exchange) chromatography using a 0–0.3M NaCl gradient. Recombinant BD1F1 and BD1F2 were analyzed by SDS-PAGE and Western blot analysis using a rabbit anti-BD1 polyclonal antibody and was compared to native BD1 (FIGS. 7 and 8).

Figure 9:
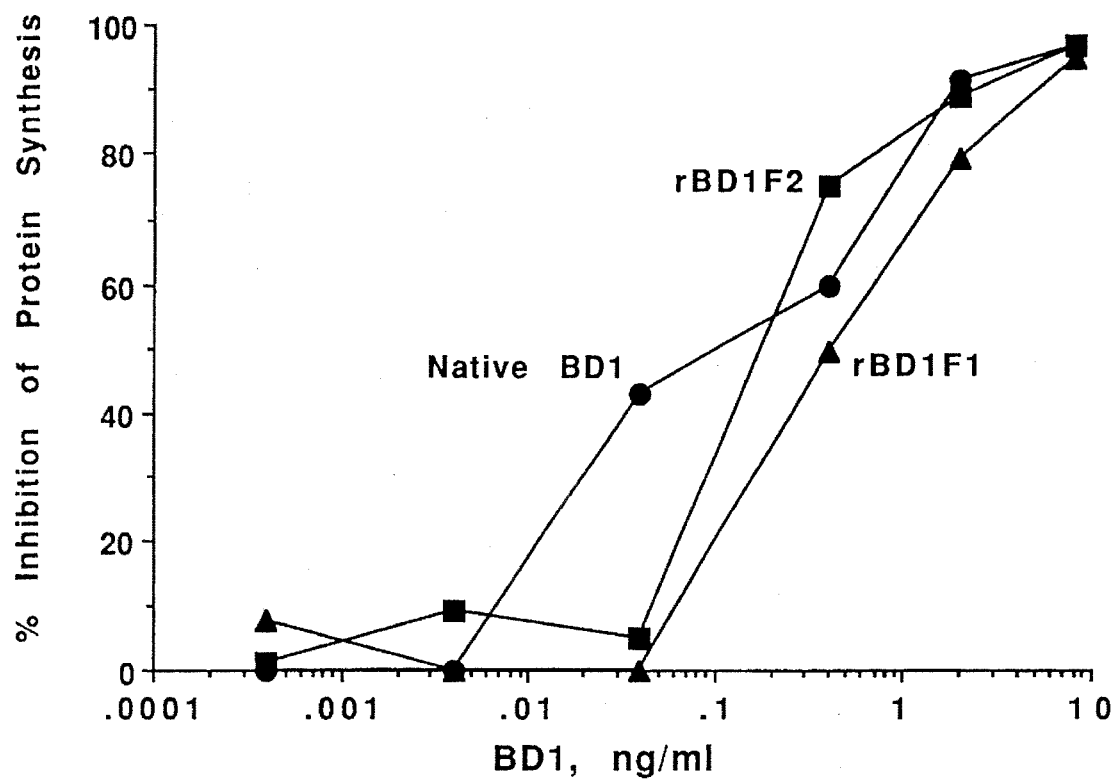
FIG. 9 provides data for protein synthesis inhibition activity of recombinant BD1F1 and BD1F2 versus native BD1 using an in vitro cell-free rabbit reticulocyte translation assay. Protein synthesis was measured as [$^3$H]-leucine incorporation of ribosome-inactivating protein treated and non-treated translation products.

Activity of the recombinant BD1 purified by both harvest methods 1 and 2 was tested in the cell-free rabbit reticulocyte assay (Promega Biotec, Madison, Wis.) which follows. Briefly, toxin proteins were mixed in a volume of 25 µl with rabbit reticulocyte lysate (70% of reaction volume), a mixture of all amino acids (minus leucine) at 1 mM, 0.5 mCi/ml [$^3$H-leucine], and Brome Mosaic Virus RNA (Shih et al. 1973. Proc. Nat'l. Acad. Sci. USA 70:1799–1803) as substrate (0.5 µg). The reaction was incubated at 30° C. for 30 min. and terminated by adding 1M NaOH, 2% $H_2O_2$. The translation product was precipitated using ice-cold 25% trichloroacetic acid (TCA), 2% casamino acids on ice for 30 min. The radiolabeled proteins were collected on glass fiber filters, rinsed with 5% TCA, rinsed with ethanol, dried, and quantitated using a scintillation counter. Recombinant BD1 isolated by both harvest methods were found to be potent inhibitors of protein synthesis and essentially equivalent to that of native BD1, with $EC_{50}$ values of 3–4 pM (FIG. 9).

We claim:

1. An isolated oligonucleotide sequence encoding a ribosome-inactivating protein from *Bryonia dioica*, the protein comprising the amino acid sequence of Sequence ID#2, or a complement of the oligonucleotide sequence.

2. The isolated oligonucleotide sequence of claim 1 comprising the nucleotide sequence of Sequence ID#1 from nucleotide number 44 to nucleotide number 913.

3. The isolated oligonucleotide sequence of claim 1 consisting of the nucleotide sequence of Sequence ID#1 from nucleotide number 113 to nucleotide number 913.

4. A recombinant vector comprising an oligonucleotide sequence encoding a ribosome-inactivating protein from *Bryonia dioica*, the protein comprising the amino acid sequence of Sequence ID#2.

5. The recombinant vector of claim 4 further comprising transcriptional and translational control sequences operably linked to the oligonucleotide sequence encoding the ribosome-inactivating protein.

6. The recombinant vector of claim 4 wherein the vector is pSE14.0 as designated ATCC 69620.

7. A host cell transfected with a recombinant vector of claim 4.

8. A host cell transfected with a recombinant vector of claim 6.

9. An isolated oligonucleotide sequence encoding a ribosome-inactivating protein from *Bryonia dioica*, the protein consisting of the amino acid sequence of Sequence ID#2 from amine acid residue number 24 to amine acid residue number 290, or a complement of the oligonucleotide sequence.

10. The isolated oligonucleotide sequence of claim 9 wherein the nucleotide sequence encodes a biologically active fragment of bryodin 1 which inhibits protein synthesis in vitro, the fragment consisting of amino acid residue sequence of Sequence ID#2 from amine acid residue number 24 to amino acid residue number 271.

11. The isolated oligonucleotide sequence of claim 10 consisting of the nucleotide sequence of Sequence ID#1 from nucleotide number 113 to nucleotide number 853.

\* \* \* \* \*